United States Patent [19]

Gosch et al.

[11] Patent Number: 5,342,488
[45] Date of Patent: Aug. 30, 1994

[54] SEPARATION OF 1,4-BUTANEDIOL FROM HYDROGENATION MIXTURES

[75] Inventors: Hans-Juergen Gosch, Bad Durkheim; Harald Rust, Neustadt; Rolf Fischer, Heidelberg; Claus Hechler, Mannheim; Rolf Pinkos, Bad Durkheim, all of Fed. Rep. of Germany

[73] Assignee: BASF Aktiengesellschaft, Ludwigshafen, Fed. Rep. of Germany

[21] Appl. No.: 18,496

[22] Filed: Feb. 17, 1993

[30] Foreign Application Priority Data

Feb. 22, 1992 [DE] Fed. Rep. of Germany ....... 4205471

[51] Int. Cl.$^5$ .................. B01D 3/00; C07C 27/00
[52] U.S. Cl. ...................... 203/80; 568/864; 568/868; 203/DIG. 19
[58] Field of Search ............... 568/864, 868; 203/80, 203/DIG. 19

[56] References Cited

U.S. PATENT DOCUMENTS 4,656,297 4/1987 Kouba et al. ............... 568/864
5,030,328 7/1991 Fischer et al. .............. 568/864

Primary Examiner—Johann Richter
Assistant Examiner—Rebecca Cook
Attorney, Agent, or Firm—Keil & Weinkauf

[57] ABSTRACT

A process for the separation of 1,4-butanediol from mixtures obtained by the catalytic hydrogenation of maleates, fumarates, and/or succinates, which also contain tetrahydrofuran, water, $C_1$–$C_4$ alcohols, succinic diesters, hydroxybutyrates, alkylhydroxyalkyl succinates, gamma-butyrolactone and butyrates, in addition to 1,4-butanediol, comprising the following steps:

a) separating, in a first column having an actual number of plates of from 20 to 70 and operated at a top pressure of from 50 to 1100 mbar and preferably from 50 to 500 mbar and a top temperature of from 40° to 120° C., alcohol, water and tetrahydrofuran, as overhead product, b) feeding the bottom product of the first column into a second column having an actual number of plates of from 30 to 90 and withdrawing the overhead product consisting of alcohol and butyrate and obtained at a top pressure of from 45 to 250 mbar and a top temperature of from 45° to 120° C., and withdrawing gamma-butyrolactone and butyrates through a side outlet, and feeding the bottom product to a phase separator, c) feeding the 1,4-butanediol-enriched bottom phase of the liquid two-phase mixture coming from the phase separator to a third column having an actual number of plates of from 30 to 90, alcohol being distilled off as overhead product at a top pressure of from 45 to 250 mbar and a top temperature of from 45° to 120° C., and the azeotrope comprising 1,4 -butanediol and succinic diester is withdrawn as a sidestream and recycled to the phase separator, whilst 1,4-butanediol is removed together with alkyl-hydroxyalkyl succinate, butyl hydroxybutyrate, and high-boiling fractions as bottoms, and d) separating the succinate-enriched top phase in the phase separator.

2 Claims, 1 Drawing Sheet

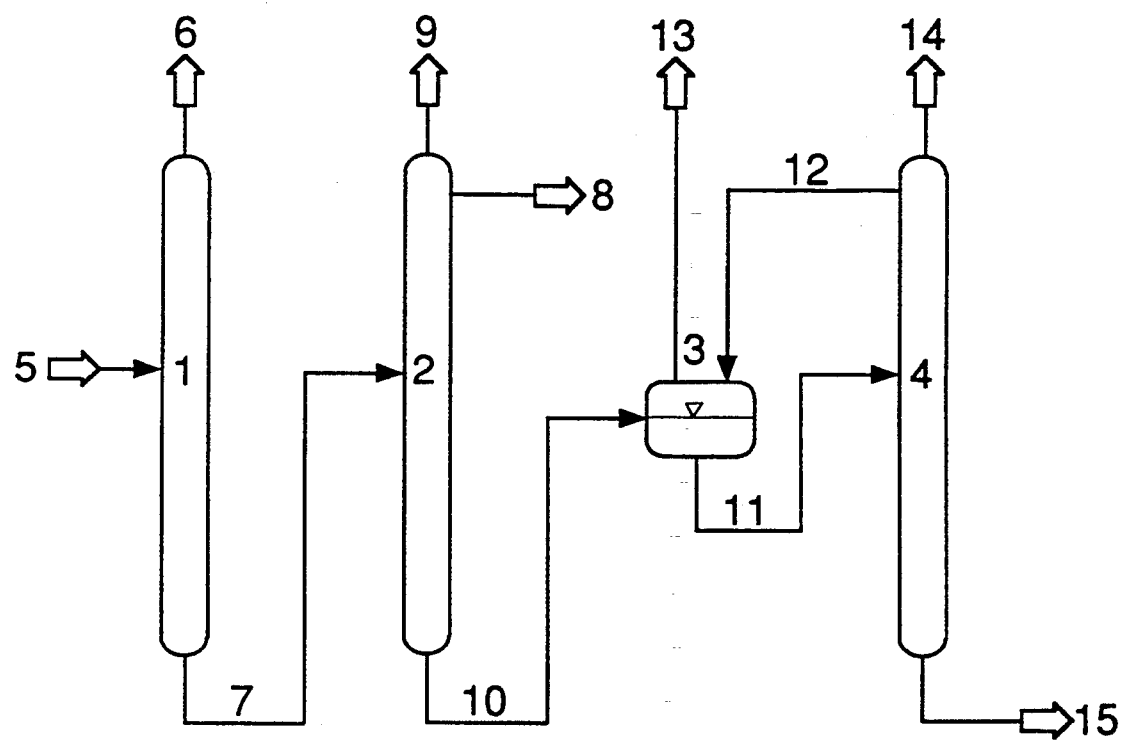

SEPARATION OF 1,4-BUTANEDIOL FROM HYDROGENATION MIXTURES

The invention relates to a process for the separation of 1,4-butanediol from mixtures obtained by the catalytic hydrogenation of maleates, fumarates, and/or succinates, which also contain tetrahydrofuran, water, $C_1$–$C_4$ alcohols, succinic diesters, hydroxybutyrates, alkyl-hydroxyalkyl succinates, gamma-butyrolactone and butyrates, in addition to 1,4-butanediol.

1,4-Butanediol, an important starting point for the synthesis of polyesters, is manufactured for example by the hydrogenation of the diethyl esters of maleic acid, fumaric acid or succinic acid (EP 143,034). Such processes produce mixtures which chiefly consist of 1,4-butanediol (BD) in addition to gamma-butyrolactone (GBL), tetrahydrofuran (THF), diethyl succinate, ethanol, n-butanol, water and minor quantities of high-boiling by-products.

It is also possible to prepare BD solutions by using maleic anhydride in excess alcohols (EP 304,696). In the hydrogenation of maleic anhydride, for example in n-butanol, the initially formed monobutyl maleate is converted to mixtures which mainly consist of BD, GBL, THF, dibutyl succinate (DBS), n-butanol, water and small quantities of high-boiling fractions.

It is thus an object of the invention to separate the 1,4-butanediol from such hydrogenation mixtures and to obtain the other desired products GBL, THF, and DBS either in pure form or in a form suitable for recycling to the hydrogenation stage if desired.

The alcohols contained in these mixtures can be $C_1$–$C_4$ alcohols such as methanol, ethanol, n-propanol, isopropanol, and/or the four isomeric butanols. Accordingly, they can contain esters derived from $C_4$ dioic acids and the said $C_1$–$C_4$ alcohols.

Hydrogenation mixtures which contain n-propanol or isopropanol and accordingly n-butyl or isobutyl carboxylate are particularly suitable for separation.

According to the invention, the above object is achieved by a) separating, in a first column having an actual number of plates of from 20 to 70 and operated at a top pressure of 50 to 1100 mbar and preferably from 50 to 500 mbar and a top temperature of from 40° to 120° C., alcohol, water and tetrahydrofuran, as overhead product, b) feeding the bottom product of the first column into a second column having an actual number of plates of from 30 to 90, removing the overhead product consisting of alcohol and butyrate and obtained at a top pressure of from 45 to 250 mbar and a top temperature of from 45° to 120° C., withdrawing gamma-butyrolactone and butyrates through a side outlet, and feeding the bottom product to a phase separator, c) feeding the 1,4-butanediol-enriched bottom phase of the liquid two-phase mixture as separated in the phase separator to a third column having an actual number of plates of from 30 to 90, alcohol being distilled off as overhead product at a top pressure of from 45 to 250 mbar and a top temperature of from 45° to 120° C., and the azeotrope comprising 1,4-butanediol and succinic diester is withdrawn as a sidestream and recycled to the phase separator, whilst 1,4-butanediol is removed together with alkyl-hydroxyalkyl succinate, butyl hydroxybutyrate, and high-boiling fractions as bottoms, and d) separating the succinate-enriched top phase in the phase separator.

The process of the invention and its essential features are illustrated in the attached drawing (simplified diagram), and are described below in more detail with reference to the use of n-butanol, by way of example.

BRIEF DESCRIPTION OF THE DRAWING

A mixture 5, consisting of 1,4-butanediol, tetrahydrofuran, water, $C_1$–$C_4$ alcohols, succinic diesters, hydroxybutyrates, alkylhydroxyalkyl succinates, gamma-butyrolactone or butyrates, obtained by the catalytic hydrogenation of maleates, fumarates, and/or succinates in a hydrogenator (not shown), is fed to a first column 1 having an actual number of plates of from 20 to 70, an overhead product 6, consisting of THF, water and more than 80% of the $C_1$–$C_4$ alcohol not chemically combined in the mixture, the bottoms 7 of the first column are fed to approximately the mid-point of a second column 2 which has an approximate number of plates of from 30 to 90, a mixture consisting of gamma butyrolactone, butyl succinate and n-butanol formed during distillation, is distilled off as an overhead product stream 9, the bottom product 10 of the second column is passed to a phase separator 3 wherein two liquid phases are formed when cooled, the top phase 13 is separated and the bottom phase 11 which mainly comprises 1,4-butanediol and small amounts of butyl hydroxybutyrate and butyl-hydroxybutyl succinate is fed into a third column 4 having 30 to 90 actual plates, newly formed n-butanol is separated as overhead product stream 14, an azeotrope of 1,4-butanediol/dibutylsuccinate is recycled to the separator 3, via a side outlet 12, together with residual and newly formed gamma butyrolactone, the effluent bottoms 15 comprise 1,4-butanediol contaminated with butyl hydroxybutyrate, butyl-hydroxybutyl succinate, and high-boiling fractions. To the first column 1 having an actual number of plates of from 20 to 70 there is fed a hydrogenation mixture 5, consisting of mixtures obtained from maleates, fumarates, and/or succinates, which contain, in addition to 1,4-butanediol, the following substances: tetrahydrofuran, water, n-butanol, succinic diesters, hydroxybutyrates, alkyl-hydroxyalkyl succinates, gamma-butyrolactone, and butyrates.

From this mixture there are distilled off, as overhead product 6, THF, water, and more than 80%, preferably 89–99%, of the butanol not chemically combined in the mixture. The temperatures and pressures at the top are for example from 40° to 100° C. and from 50 to 500 mbar. The reflux ratio is between 0.1 and 0.8.

The overhead product from the first column, a mixture of THF, water, and butanol, can be worked up in known manner to give pure THF. Water is removed, and the butanol is recycled to the hydrogenation process.

The bottoms 7 of the first column are fed to approximately the mid-point of a second column 2 which has an actual number of plates ranging from 30 to 90 and in which the overhead product stream 9 comprises GBL, butyl succinate (BS), as well as n-butanol mainly formed during distillation. In a side outlet 8 there are separated residues of BS and more than 80% of the GBL contained in the mixture. During this operation the top temperature is from 45° to 120° C. under a pressure of from 45 to 250 mbar. The reflux ratio is, e.g., from 3 to 15.

The n-butanol produced as overhead product in the second column can also be recycled, if desired following separation of butyl butyrate, to the hydrogenation stage.

The GBL obtained in the side outlet of the second column can be purified and used for example for the preparation of N-methylpyrrolidone, or, if desired, recycled to the hydrogenation.

The bottom product 10 of the second column is passed to a phase separator 3. On cooling, the bottom product forms two liquid phases. The top phase 13 contains chiefly DBS, which is separated, and can be recycled, for example, to the hydrogenation stage. The bottom phase 11, which mainly comprises BD and small amounts of butyl hydroxybutyrate (BHOB) and butylhydroxybutyl succinate (B-HOBS), is fed into a third column 4 having from 30 to 90 actual plates. At a top temperature of from 45° to 120° C. and a top pressure of from 45 to 250 mbar, newly formed butanol is separated as overhead product stream 14. Via a side outlet 12, the BD/DBS azeotrope is recycled to the separator together with residual and newly formed GBL. The effluent bottoms 15 comprise BD contaminated with BHOB, B-HOBS, and high-boiling fractions. The reflux ratio is, e.g., from 30 to 50. The BD thus obtained can be treated in known manner by distillation to provide pure BD.

The mixtures containing BD and used for the novel process are formed, for example, by the catalytic hydrogenation of the butyl esters of maleic acid, fumaric acid and/or succinic acid. They can have, for example the following composition: from 10 to 70 wt % of butanol, from 0.5 to 10 wt % of THF, from 1.5 to 9 wt % of water, from 2 to 15 wt % of GBL, from 20 to 50 wt % of BD, from 2 to 15 wt % of DBS, from 0.1 to 4 wt % of BS, from 0.01 to 3 wt % of BHOB, from 0.01 to 3 wt % of B-HOBS, and from 0.01 to 5 wt % of high-boiling fractions.

The process of this invention allows 1,4-butanediol to be very readily separated from hydrogenation mixtures.

It is known from a prior disclosure in EP 169,396 that mixtures of BD and DBS break down at temperatures below 108° C. to form two liquid phases: a BD-enriched bottom phase and a DBS-enriched top phase. However, no predictions could have been made as to whether the BD/DBS mixtures containing further components would be capable of adequate, industrially utilizable phase separation.

EXAMPLE

The hydrogenation mixture awaiting rectification had the following composition: 1.9% of THF, 58.9% of n-butanol, 2.0% of GBL, 23.1% of BD, 0.4% of BS, 0.3% of BHOB, 6.4% of DBS and 0.5% of B-HOBS, 0.5% of high-boiling fractions, and 6.0% of water.

The process is illustrated by the attached drawing. Through the inlet (5) there are fed 100 parts of the mixture into the first column (1). The column has 35 theoretical plates. At a top temperature of 68° C. and a top pressure of 115 mbar the product obtained comprises, at a reflux ratio of 0.5, 66 parts of an overhead product (6) composed of 2.9% of THF, 89.2% of butanol, and 7.9% of water. The bottom product (7) comprises 34 parts of a mixture of 1.4% of n-butanol, 5.9% of GBL, 67.9% of BD, 1.2% of BS, 0.9% of BHOB, 1.5% of high-boiling fractions, 18.8% of DBS, 1.5% of B-HOBS and 0.9% of other compounds.

100 parts of bottom product (7) from the first column are passed to the second column (2) having 35 theoretical plates. At a top temperature of 65° C., a top pressure of 100 mbar and a reflux ratio of 10, 15 parts of overhead product (9) are obtained having the following composition: 82% n-butanol, 5.7% of GBL, 6.5% of BS and water, and 7 parts of sidestream (8) coming from the enriching zone and composed of 7% n-butanol, 77.4% of GBL, 9.3% of BD, 2.8% of BS, and 3.5% of DBS. The bottom product (10) comprises 78 parts of a mixture of 0.2% of GBL, 71.7% of BD, 0.5% of BHOB, 9.3% of DBS, and 16.4% of B-HOBS and 1.9% of high-boiling fractions.

The bottom product (10) is passed to the phase separator (3).

100 parts of bottom phase (11) from the phase separator are passed to the third column (4) having 35 theoretical plates. At a top temperature of 46° C., a top pressure of 100 mbar and a reflux ratio of 40, there are obtained 4 parts of overhead product (14) having the following composition: 76% of n-butanol and 24% of water, and 16 parts of sidestream (12) from the enriching zone, this being composed of 2% of n-butanol, 2% of GBL, 61% of BD, 33% of DBS, and 2% of other compounds. The bottom product (15) obtained comprises 80 parts of a mixture of 90.5% of BD, 5.5% of B-HOBS, and 4% of high-boiling fractions.

The sidestream (12) is passed to the phase separator (3).

The bottom product (10) and sidestream (12) are blended in the phase separator (3). Phase separation makes it possible to withdraw a top phase (13), mainly consisting of DBS, which is returned to the hydrogenation stage. The bottom phase (11), which consists of BD, BHOB, DBS, high-boiling fractions, and B-HOBS, is passed to the third column.

We claim:

1. A process for the separation of 1,4-butanediol from a mixture obtained by the catalytic hydrogenation of maleates, fumarates, and/or succinates, which mixture also contains tetrahydrofuran, water, $C_1$–$C_4$ alcohols, succinic diesters, hydroxybutyrates, alkylhydroxyalkyl succinates, gamma-butyrolactone or butyrates, in addition to 1,4-butanediol, comprising the following steps:
   a) separating, in a first column having an actual number of plates of from 20 to 70 and operated at a top pressure of from 50 to 1100 mbar and a top temperature of from 40° to 120° C., the $C_1$–$C_4$ alcohols, water and tetrahydrofuran, as overhead product,
   b) feeding the bottom product of the first column into a second column having an actual number of plates of from 30 to 90 and withdrawing the overhead product consisting of alcohol and butyrate and obtained at a top pressure of from 45 to 250 mbar and a top temperature of from 45° to 120° C., and withdrawing the gamma-butyrolactone and butyrates through a side outlet, and feeding the bottom product to a phase separator,
   c) feeding the 1,4-butanediol-enriched bottom phase of the liquid two-phase mixture coming from the phase separator to a third column having an actual number of plates of from 30 to 90, alcohol being distilled off as overhead product at a top pressure of from 45 to 250 mbar and a top temperature of from 45° to 120° C., and an azeotrope comprising the 1,4-butanediol and succinic diesters is withdrawn as a sidestream and recycled to the phase separator while the 1,4-butanediol is removed together with the alkylhydroxyalkyl succinates, hydroxybutyrates and high-boiling fractions as bottoms, and
   d) separating the alkylhydroxyalkyl succinates-enriched top phase in the phase separator.

2. A process as claimed in claim 1, wherein the alcohol components of the carboxylates are derived from $C_1$–$C_4$ alcohols.

* * * * *